United States Patent
Li et al.

(10) Patent No.: US 11,926,774 B1
(45) Date of Patent: Mar. 12, 2024

(54) HYDROGEN-BONDED ORGANIC FRAMEWORK NANOSHEET, PREPARATION METHOD AND APPLICATION THEREOF

(71) Applicant: Yantai University, Shandong (CN)

(72) Inventors: Zhongyue Li, Shandong (CN); Xinxin Zhang, Shandong (CN); Kun Liu, Shandong (CN); Wei Liu, Shandong (CN)

(73) Assignee: YANTAI UNIVERSITY, Shandong (CN)

(*) Notice: Subject to any disclaimer, the term of this patent is extended or adjusted under 35 U.S.C. 154(b) by 0 days.

(21) Appl. No.: 18/474,008

(22) Filed: Sep. 25, 2023

(30) Foreign Application Priority Data

Sep. 26, 2022 (CN) .......................... 202211176768.5

(51) Int. Cl.
  *C09K 11/07* (2006.01)
  *C07C 235/88* (2006.01)
  *G01N 21/64* (2006.01)

(52) U.S. Cl.
  CPC ............ *C09K 11/07* (2013.01); *C07C 235/88* (2013.01); *G01N 21/643* (2013.01); *C09K 2211/1007* (2013.01); *G01N 2021/6432* (2013.01)

(58) Field of Classification Search
  None
  See application file for complete search history.

(56) References Cited

FOREIGN PATENT DOCUMENTS

| CN | 106632433 A | 5/2017 |
|----|-------------|--------|
| CN | 113201144 A | 8/2021 |
| CN | 114262444 A | 4/2022 |
| CN | 115073756 A | 9/2022 |
| WO | 2020252536 A1 | 12/2020 |

OTHER PUBLICATIONS

Ding, X, et al. Binary Solvent Regulated Architecture of Ultra-Microporous Hydrogen-Bonded Organic Frameworks with Tunable Polarization for Highly-Selective Gas Separation, Angew. Chem. Int. Ed. 2022, 61, e202116483 (Year: 2022).*
Notification to Grant Patent Right for Invention from SIPO in application No. 202211176768.5 dated Jun. 29, 2023.

(Continued)

*Primary Examiner* — Xiaoyun R Xu
(74) *Attorney, Agent, or Firm* — Pilloff Passino & Cosenza LLP; Rachel K. Pilloff; Sean A. Passino

(57) ABSTRACT

A hydrogen-bonded organic framework nanosheet, a preparation method and application thereof are provided. The preparation method includes in a small heat-resistant glass container, mixing 1,2,4,5-tetrakis (4-carboxyphenyl) benzene ($H_4TCPB$) with N,N-dimethylformamide (DMF), heating until the solid is dissolved, placing the uncapped small glass container in a large heat-resistant glass container filled with some water, sealing the large glass container, standing and heating the large glass container in a constant-temperature oven to obtain colorless crystals, suction filtering to obtain a solid material, drying, grinding, and then dispersing the solid material in a solvent, performing ultrasonication in an ice-water bath, centrifuging to discard supernatant, and drying to obtain the hydrogen-bonded organic framework nanosheets.

6 Claims, 20 Drawing Sheets

(56) References Cited

OTHER PUBLICATIONS

Retrieval report from SIPO in application No. 202211176768.5 dated May 10, 2023.
Retrieval report from SIPO in application No. 202211176768.5 dated Jun. 25, 2023.
Notice of the First Office Action from SIPO in application No. 202211176768.5 dated May 11, 2023.

* cited by examiner

● = *N,N*-dimethylformamide

● = *N,N*-dimethylformamide

HYDROGEN-BONDED ORGANIC FRAMEWORK NANOSHEET, PREPARATION METHOD AND APPLICATION THEREOF

CROSS-REFERENCE TO RELATED APPLICATIONS

This application claims priority of Chinese Patent Application No. 202211176768.5, filed on Sep. 26, 2022, the entire contents of which are incorporated herein by reference.

TECHNICAL FIELD

The application relates to a hydrogen-bonded organic framework nanosheet, a preparation method and an application thereof, and belongs to the technical fields of material science, environmental science and synthesis.

BACKGROUND

Hydrogen-bonded organic frameworks (HOFs) are crystalline porous materials constructed by intermolecular hydrogen bonding of organic structural units, also known as supramolecular organic frameworks (SOFs), etc. Because of unique physical and chemical properties of the hydrogen-bonded organic frameworks, it has made important progress in the fields of gas storage and separation, proton conduction, biomedicine, molecular recognition, heterogeneous catalysis and so on. In recent years, the structural design and application development of metal-organic frameworks (MOFs) and covalent organic frameworks (COFs) have received extensive attention. At the beginning of rapid development of the MOFs and the COFs, HOFs, as a similar crystalline porous material, are greatly "underestimated". This is because the bonding bond of HOFs is hydrogen bond, which is relatively weak, and the HOFs are often unable to maintain a stable porous framework after guest molecules are removed, and the directivity of HOFs is poor, so it is difficult to accurately predict the synthesized target structure.

In recent ten years, scientists have found that by reasonably designing and selecting structural units, establishing multiple hydrogen bonds, and introducing other intermolecular forces such as interpenetrating interlocking, π-π stacking, electrostatic interaction, van der Waals force, etc., the stability of HOFs is capable of being effectively improved, and HOFs materials with stable framework are capable of being obtained. Therefore, some structurally stable HOFs materials have been developed, and their excellent properties in gas storage and separation, heterogeneous catalysis, biological application and sensor analysis have been studied. However, at present, the development of synthesis methods of stable HOFs materials focuses on the microstructure design, including the design of organic monomer geometry, the expansion of hydrogen bonding mode, the construction of interpenetrating structure and the introduction of π-π stacking and other interactions, while the research and discussion on the influence of temperature on the structure of HOFs are relatively few.

The rapid development of nuclear power is accompanied by the discharge of radioactive waste water containing uranium produced by nuclear fuel processing and production, a large amount of uranium isotope waste produced during nuclear fuel consumption and uranium pollution caused by nuclear leakage. As the most stable chemical substance containing uranyl ions is extremely soluble in water and has radioactivity and chemical toxicity. Uranyl ions entering the ecosystem will be enriched in water and soil, and once they contact or enter the human body, they will cause irreversible damage to human organs. At present, uranyl ions in water may be directly detected by Inductively Coupled Plasma-Mass Spectrometry (ICP-MS), ion chromatography, laser-induced kinetic phosphorescence analysis and radioactivity measurement. However, although these methods have high accuracy, they are usually expensive and very demanding in sample preparation and instrument operation.

Fluorescent probe is a portable, sensitive and economical detection method, which has a good application prospect in the field of uranyl detection in water.

SUMMARY

In order to solve the above technical problems, the application provides a hydrogen-bonded organic framework nanosheet, and a preparation method and application thereof. Accord to the application, the influence of crystallization temperature on the thermal motion of solvent molecules is utilized, and the hydrogen bonding association of solvent molecules in HOFs crystals is controlled by adjusting the crystallization temperature, so that the hydrogen-bonded organic framework material with stable double hydrogen bonding and double-interpenetrating plane network structure is synthesized. Through simple temperature control, the preparation of highly stable two-dimensional HOFs is realized, and the hydrogen-bonded organic framework material is exfoliated into ultra-thin nanosheet with uniform thickness. On the one hand, based on the fluorescent properties of monomers, the HOFs material is endowed with fluorescent properties; on the other hand, the weak intermolecular force in the HOFs and the interpenetrating network structure make the material easy to be exfoliated into a nano-sheet structure, and have good fluorescence response sensitivity of uranyl, so the HOFs material may be used as a fluorescent probe for detecting uranyl.

In order to achieve the above objectives, the present application provides the following scheme.

The application provides a preparation method of a hydrogen-bonded organic framework nanosheet, including the following steps:

in a small heat-resistant glass container, mixing 1,2,4,5-tetrakis (4-carboxyphenyl) benzene ($H_4TCPB$) with N,N-dimethylformamide (DMF), dissolving the solid by heating, placing the uncapped small glass container filled with $H_4TCPB$ and DMF in a large heat-resistant glass container filled with water, sealing the large glass container, standing and heating the large glass container in a constant-temperature oven, suction filtering to obtain colorless crystals, and then drying the colorless crystals to obtain a solid material, grinding and dispersing the solid material in a solvent, performing ultrasonication in an ice-water bath, centrifuging to discard supernatant, and finally drying to obtain the hydrogen-bonded organic framework nanosheet.

Optionally, 1,2,4,5-tetrakis (4-carboxyphenyl) benzene ($H_4TCPB$) is mixed with N, N-dimethylformamide (DMF), and the solid is dissolved by heating, so the concentration of 1,2,4,5-tetrakis (4-carboxyphenyl) benzene is 1-50 mg/mL.

Optionally, the temperature for the standing and heating is more than or equal to 100° C.

Optionally, the time for standing is 1-7 days.

Optionally, after suction filtering to obtain colorless crystals, the temperature for drying is 60-200° C."

Optionally, the solvent includes one or more of ethanol, water, methanol and isopropanol.

The application also provides a hydrogen-bonded organic framework nanosheet prepared by the above preparation method. The crystal structure of the hydrogen-bonded organic framework nanosheet belongs to monoclinic system, C2/c space group, and the cell parameters are a=22.5168, b=11.3785, c=20.8639, $\alpha$=90, $\beta$=96.783, $\gamma$=90. All carboxyl groups in the micro-crystal structure are connected by double hydrogen bonds, and the layered networks of double rhomboids are interpenetrated with each other to form a dense and stable two-dimensional layered structure.

The application also provides a fluorescent probe, which is prepared by the hydrogen-bonded organic framework nanosheet mentioned above.

A preparation method of the fluorescent probe includes the following steps: grinding the hydrogen-bonded organic framework nanosheet for 10 minutes, placing in the solvent, and ultrasonically dispersing for 1-10 minutes to obtain a fluorescent probe with a concentration of 10-200 mg/L.

Optionally, in the preparation method of the fluorescent probe, the solvent includes one or more of water, ethanol and methanol.

The application also provides an application of the hydrogen-bonded organic framework nanosheet or the fluorescent probe or the preparation method of the fluorescent probe in detecting uranyl ions.

The application discloses the following technical effects.

Firstly, under the same raw materials, solvents and synthetic conditions, according to the application, the thermal motion of solvent DMF molecules is controlled in the crystallization process of HOFs through simple temperature adjustment: with the increase of temperature, the thermal motion of DMF molecules gradually intensifies, reducing the possibility of forming hydrogen bonds with monomer $H_4$TCPB. At 25° C., all four carboxyl groups on $H_4$TCPB monomer form hydrogen bonds with DMF molecules, but the monomers are independent of each other and have no hydrogen bonds. When the temperature is raised to 60° C., the carboxyl groups on $H_4$TCPB monomer are linked to each other through unilateral hydrogen bonds, and the other —OH forms hydrogen bonds with DMF. When the temperature reaches 100° C. or above, DMF molecules no longer participate in the hydrogen bond network of HOFs, and stable double hydrogen bonds are formed between carboxyl groups of monomers in a head-to-head manner.

Secondly, because there is no solvent in the crystal structure of the hydrogen-bonded organic framework nanosheet prepared by the application, the structural units are connected by stable double hydrogen bonds to form a layered structure with a rhombic network, and the double networks are interpenetrated with each other to form dense two-dimensional layers, and the layers are stacked by weak π-π interaction. The unique structural characteristics endow the material with the following properties: on the one hand, there is strong interaction within the layers, which has high thermal stability and chemical stability; on the other hand, the interaction between the layers is weak and easy to exfoliated from each other. After ultrasonic exfoliating, ultra-thin nanosheet with uniform thickness of about 1.5 nm are obtained.

Lastly, when encountering uranyl ions, the nano fluorescent probe prepared by the hydrogen-bonded organic framework nanosheet has a sensitive fluorescence quenching effect, the fluorescence emission intensity is decreased with the increase of uranyl ion concentration, and the detection limit of uranyl ions is as low as 0.13 g/L. The instruments used in the preparation method of the nanosheet are common in the laboratory and easy to operate, and the exfoliating process is simple, the cost is low, and the preparation process causes less environmental pollution. The preparation process and instrument of fluorescent probe are simple, and the sensitivity of detecting uranyl ions is high, which has broad application prospects.

BRIEF DESCRIPTION OF THE DRAWINGS

In order to explain the embodiments of the present application or the technical scheme in the prior art more clearly, the drawings needed in the embodiments will be briefly introduced below. Obviously, the drawings in the following description are only some embodiments of the present application. For ordinary people in the field, other drawings may be obtained according to these drawings without paying creative labor.

DETAILED DESCRIPTION OF THE EMBODIMENTS

Figure 1:
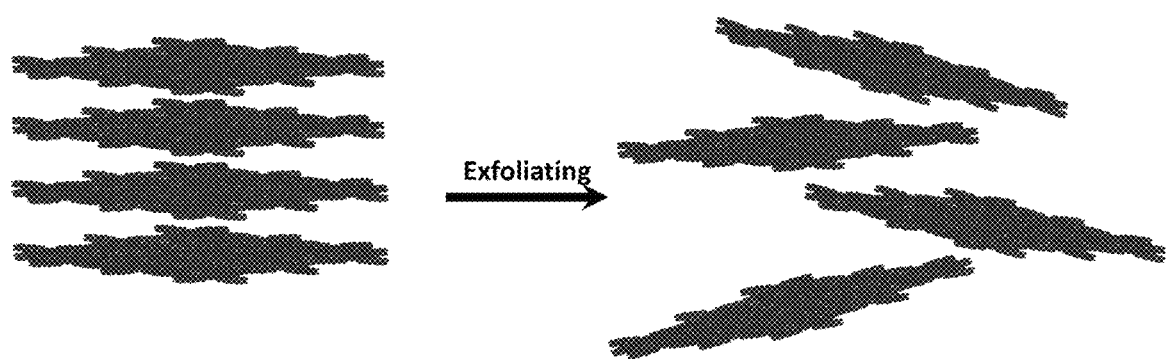
FIG. 1 is a schematic diagram of a process of obtaining a hydrogen-bonded organic framework nanosheet after a hydrogen-bonded organic framework is exfoliated in an embodiment of the present application.

A number of exemplary embodiments of the present application will now be described in detail, and this detailed description should not be considered as a limitation of the present application, but should be understood as a more detailed description of certain aspects, characteristics and embodiments of the present application.

It should be understood that the terminology described in the present application is only for describing specific embodiments and is not used to limit the present application. In addition, for the numerical range in the present application, it should be understood that each intermediate value between the upper limit and the lower limit of the range is also specifically disclosed. The intermediate value within any stated value or stated range and every smaller range between any other stated value or intermediate value within the stated range are also included in the present application. The upper and lower limits of these smaller ranges may be independently included or excluded from the range.

Unless otherwise specified, all technical and scientific terms used herein have the same meaning as commonly understood by one of ordinary skill in the art to which this application relates. Although the present application only describes the preferred methods and materials, any methods and materials similar or equivalent to those described herein may also be used in the practice or testing of the present application. All documents mentioned in this specification are incorporated by reference to disclose and describe methods and/or materials related to the documents. In case of conflict with any incorporated document, the contents of this specification shall prevail.

It is obvious to those skilled in the art that many improvements and changes may be made to the specific embodiments of the present application without departing from the scope or spirit of the present application. Other embodiments will be apparent to the skilled person from the description of the application. The description and embodiments of that present application are exemplary only.

The terms "including", "having" and "containing" used in this article are all open terms, which means including but not limited to.

Embodiments of the present application provide a preparation method of a hydrogen-bonded organic framework nanosheet, including the following steps:

in a small heat-resistant glass container, mixing 1,2,4,5-tetrakis (4-carboxyphenyl) benzene ($H_4TCPB$) with N,N-dimethylformamide (DMF), dissolving the solid by heating, placing the uncapped small glass container filled with $H_4TCPB$ and DMF in a large heat-resistant glass container filled with water, sealing the large glass container, standing and heating the large glass container in a constant-temperature oven, suction filtering to obtain colorless crystals, and then drying the colorless crystals to obtain a solid material, grinding and dispersing the solid material in a solvent, performing ultrasonication in an ice-water bath, centrifuging to discard supernatant, and finally drying to obtain the hydrogen-bonded organic framework nanosheet.

In embodiments of the present application, the solid material is a hydrogen-bonded organic framework. The solid material is subjected to grinding, and ultrasonic treatment in the solvent to realize exfoliating of the hydrogen-bonded organic framework nanosheet. The process of exfoliating is shown in FIG. 1.

In embodiments of the present application, 1,2,4,5-tetrakis (4-carboxyphenyl) benzene is mixed with N, N-dimethylformamide, and the solid is dissolved by heating, so the concentration of 1,2,4,5-tetrakis (4-carboxyphenyl) benzene is 1-50 mg/mL.

In embodiments of the present application, the temperature for heating is more than or equal to 100° C., such as 100° C., but not limited to 100° C.

In embodiments of the present application, the time for standing is 1-7 days.

In embodiments of the present application, after suction filtering to obtain colorless crystals, the temperature for drying is 60-200° C.

In embodiments of the present application, the solvent includes one or more of ethanol, water, methanol and isopropanol.

The embodiments of the present application also provide a hydrogen-bonded organic framework nanosheet prepared by the above preparation method. The crystal structure of the hydrogen-bonded organic framework nanosheet belongs to monoclinic system, C2/c space group, and the cell parameters are a=22.5168, b=11.3785, c=20.8639, α=90, β=96.783, γ=90. All carboxyl groups in the micro-crystal structure are connected by double hydrogen bonds, and the layered networks of double rhomboids are interpenetrated with each other to form a dense and stable two-dimensional layered structure.

The embodiment of the present application also provides a fluorescent probe. The fluorescent probe is prepared by using the hydrogen-bonded organic framework nanosheet mentioned above.

A preparation method of the fluorescent probe provided in embodiments of present application includes the following steps: grinding the hydrogen-bonded organic framework nanosheet for 10 minutes, placing in the solvent, and ultrasonically dispersing for 1-10 minutes to obtain a fluorescent probe with a concentration of 10-200 mg/L.

In the embodiments of the application, in the preparation method of the fluorescent probe, the solvent includes one or more of water, ethanol and methanol.

The embodiments of present application also provide an application of the hydrogen-bonded organic framework nanosheet or the fluorescent probe or the preparation method of the fluorescent probe in detecting uranyl ions.

All the raw materials used in the application may be purchased in the market.

The technical scheme of the present application will be further explained by embodiments.

Embodiment 1

Figure 2:
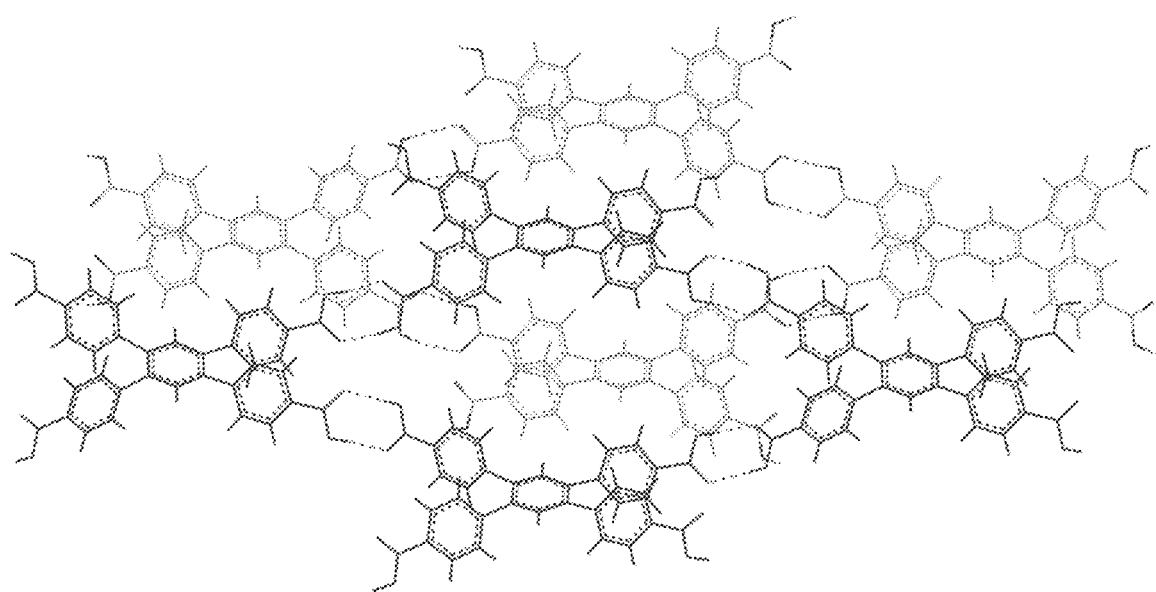
FIG. 2 is a schematic structural diagram of hydrogen-bonded organic framework nanosheet prepared in embodiment 1 of the present application.

20 mg of $H_4TCPB$ and 1 mL of DMF solution are mixed in 5 mL of small heat-resistant glass bottle, and heated to 100° C. to completely dissolve $H_4TCPB$. The uncapped small heat-resistant glass container filled with the mixture is put in 100 mL of large heat-resistant glass bottle filled with 5 mL of water, the lid of large heat-resistant glass bottle is tightened to seal the large glass bottle. The large glass bottle is standing in a constant-temperature oven at 100° C. for 2 days, and is subjected to suction filtering to obtain colorless crystals. The colorless crystals are dried in the constant-temperature oven at 60° C. to obtain a solid material. The solid material is ground for minutes, dispersed in ethanol, ultrasonically treated in an ice-water bath for 30 minutes, centrifugated to discard supernatant, and dried at 60° C. to obtain a hydrogen-bonded organic framework nanosheet. The structural schematic diagram of hydrogen-bonded organic framework nanosheet is shown in FIG. 2.

20 mg of hydrogen-bonded organic framework nanosheet prepared in embodiment 1 of the present application are ground for 10 minutes, and then dispersed in 100 mL of water for ultrasonic treatment for 10 minutes to obtain a fluorescent probe with a concentration of 200 mg/L.

Embodiment 2

5 mg of $H_4TCPB$ and 5 mL of DMF solution are mixed in 10 mL of small heat-resistant glass bottle, and heated to 80° C. to completely dissolve $H_4TCPB$. The uncapped small heat-resistant glass bottle mentioned above is put in 100 mL of large heat-resistant glass bottle filled with 10 mL of water, the lid of large heat-resistant glass bottle is tightened to seal the large glass bottle. The large glass bottle is standing in a constant-temperature oven at 100° C. for 7 days, and is subjected to suction filtering to obtain colorless crystals. The colorless crystals are dried in the constant-temperature oven at 200° C. to obtain a solid material. The solid material is ground for 10 minutes, dispersed in water, ultrasonically treated in an ice-water bath for 30 minutes, centrifugated to discard supernatant, and dried at 200° C. to obtain a hydrogen-bonded organic framework nanosheet.

Embodiment 3

50 mg of monomer $H_4TCPB$ and 1 mL of DMF solution are mixed in 5 mL of small heat-resistant glass bottle, and heated to 100° C. to completely dissolve $H_4TCPB$. The uncapped small heat-resistant glass bottle mentioned above is put in 100 mL of large heat-resistant glass bottle filled with 10 mL of water, the lid of large heat-resistant glass bottle is tightened to seal the large glass bottle. The large glass bottle is standing in a constant-temperature oven at 100° C. for 1 day, and is subjected to suction filtering to obtain colorless crystals. The colorless crystals are dried in the constant-temperature oven at 100° C. to obtain a solid material. The solid material is ground for 10 minutes, dispersed in the mixed solvent of methanol and isopropanol (volume ratio of 4:1), ultrasonically treated in an ice-water bath for 30 minutes, centrifugated to discard supernatant, and dried at 100° C. to obtain a hydrogen-bonded organic framework nanosheet.

Comparative Example 1

Figure 3:
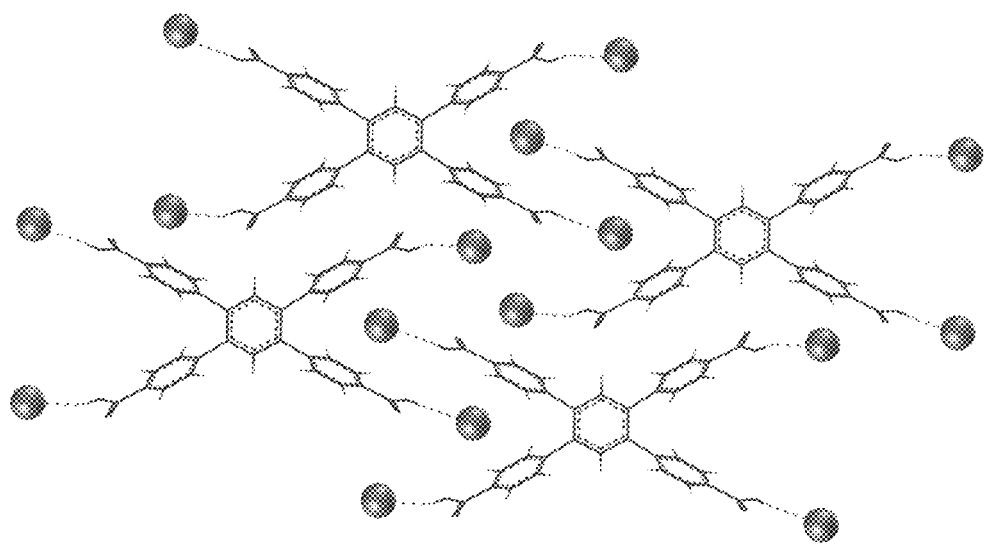
FIG. 3 is a schematic structural diagram of a crystal material prepared in comparative example 1 of the present application.

20 mg of monomer $H_4TCPB$ and 1 mL of DMF solution are mixed in 5 mL of small heat-resistant glass bottle, and heated to 100° C. to completely dissolve $H_4TCPB$. The uncapped small heat-resistant glass bottle mentioned above is put in 100 mL of large heat-resistant glass bottle filled with 10 mL of water, the lid of large heat-resistant glass bottle is tightened to seal the large glass bottle. The large glass bottle is standing in a constant-temperature oven at 25° C. for 7 day, and is subjected to suction filtering to obtain colorless crystals. The colorless crystals are dried in the constant-temperature oven at 60° C. to obtain a solid material. The solid material is ground for 10 minutes, dispersed in ethanol solvent, ultrasonically treated in an ice-water bath for 30 minutes, centrifugated to discard supernatant, and dried at 60° C. to obtain a crystal material. A schematic structural diagram of the crystal material prepared in comparative example 1 of the present application is shown in FIG. 3. It can be seen from FIG. 3 that the structure of the crystal material is different from the structure of the hydrogen-bonded organic framework nanosheet prepared in embodiment 1 of the present application.

The crystallographic data of the crystal material prepared in comparative example 1 of the present application are shown in table 1. As can be seen from table 1, the crystal material obtained in comparative example 1 has poor water stability, while the hydrogen-bonded organic framework nanosheet synthesized in embodiment 1 of the present application has good water stability.

Figure 4:
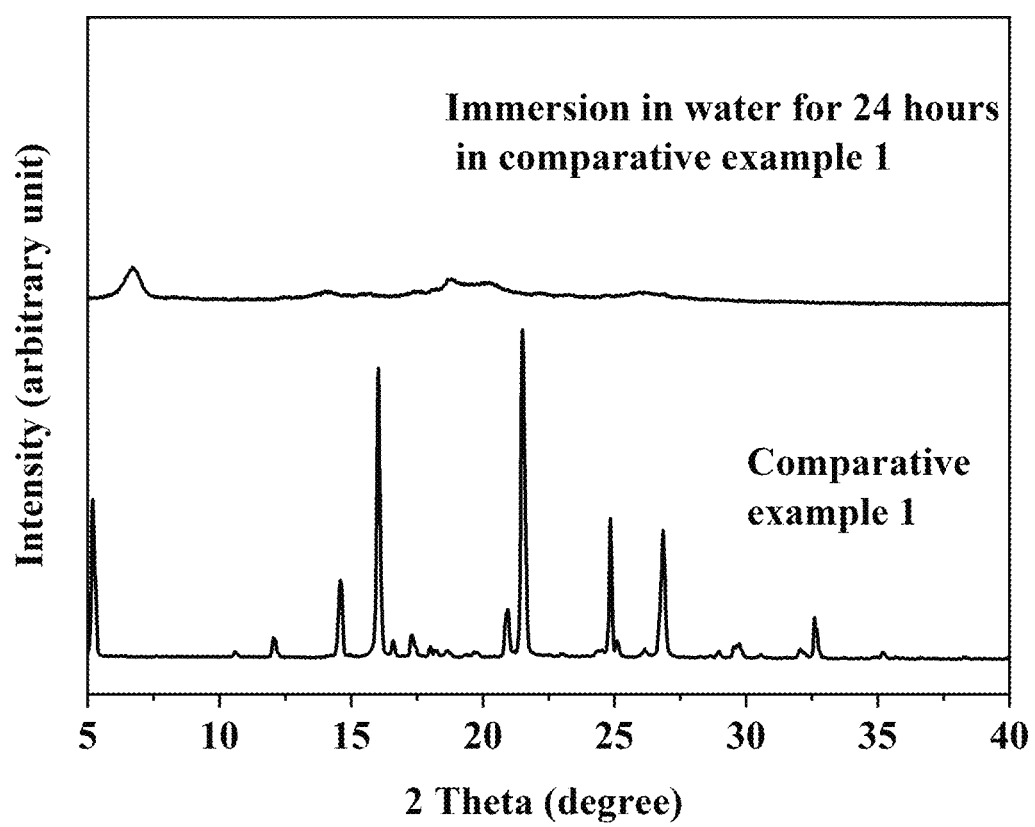
FIG. 4 is an X-ray diffraction spectrum of a crystal material prepared in comparative example 1 of the present application before and after being immersed in water for 24 hours.

The X-ray diffraction (XRD) spectrum of the crystal material prepared in comparative example 1 of the present application before and after immersion in water is shown in FIG. 4, and the results show that the crystal material is not capable of maintaining its original crystal structure after being immersed in water for 24 hours.

Comparative Example 2

Figure 5:
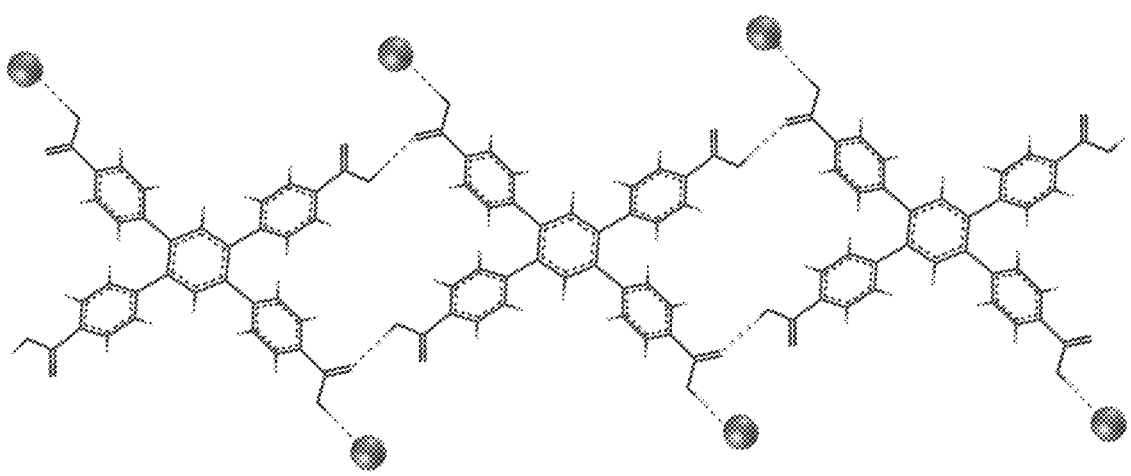
FIG. 5 is a schematic structural diagram of a crystal material prepared in comparative example 2 of the present application.

20 mg of monomer $H_4TCPB$ and 1 mL of DMF solution are mixed in 5 mL of small heat-resistant glass bottle, and heated to 100° C. to completely dissolve $H_4TCPB$. The uncapped small heat-resistant glass bottle mentioned above is put in 100 mL of large heat-resistant glass bottle filled with 10 mL of water, the lid of large heat-resistant glass bottle is tightened to seal the large glass bottle. The large glass bottle is standing in a constant-temperature oven at 60° C. for 7 days, and is subjected to suction filtering to obtain colorless crystals. The colorless crystals are dried in the constant-temperature oven at 60° C. to obtain a solid material. The solid material is ground for 10 minutes, dispersed in ethanol solvent, ultrasonically treated in an ice-water bath for 30 minutes, centrifugated to discard supernatant, and dried at 60° C. to obtain a crystal material. A schematic structural diagram of the crystal material prepared in comparative example 2 of the present application is shown in FIG. 5. It can be seen from FIG. 5 that the crystal structure of the crystal material is different from the crystal structure of the hydrogen-bonded organic framework nanosheet prepared in embodiment 1 of the present application.

The crystallographic data of the crystal material prepared in comparative example 2 of the present application are shown in table 1. As can be seen from table 1, the crystal material obtained in comparative example 2 has poor water stability, while the hydrogen-bonded organic framework nanosheet synthesized in embodiment 1 of the present application has good water stability.

Figure 6:
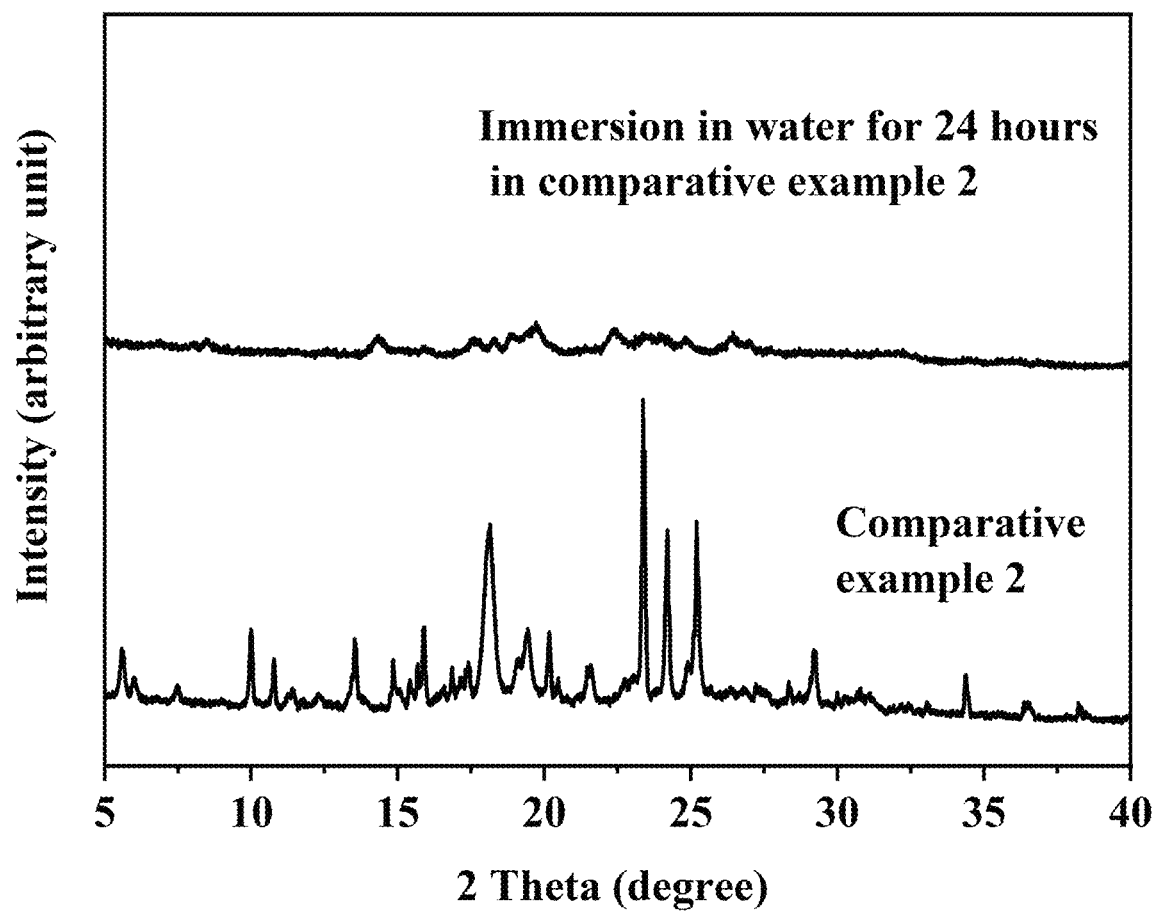
FIG. 6 is an X-ray diffraction spectrum of a crystal material prepared in comparative example 2 of the present application before and after being immersed in water for 24 hours.

The X-ray diffraction (XRD) spectrum of the crystal material prepared in comparative example 2 of the present application before and after immersion in water is shown in FIG. 6, and the results show that the crystal material is not capable of maintaining its original crystal structure after being immersed in water for 24 hours.

Figure 7:
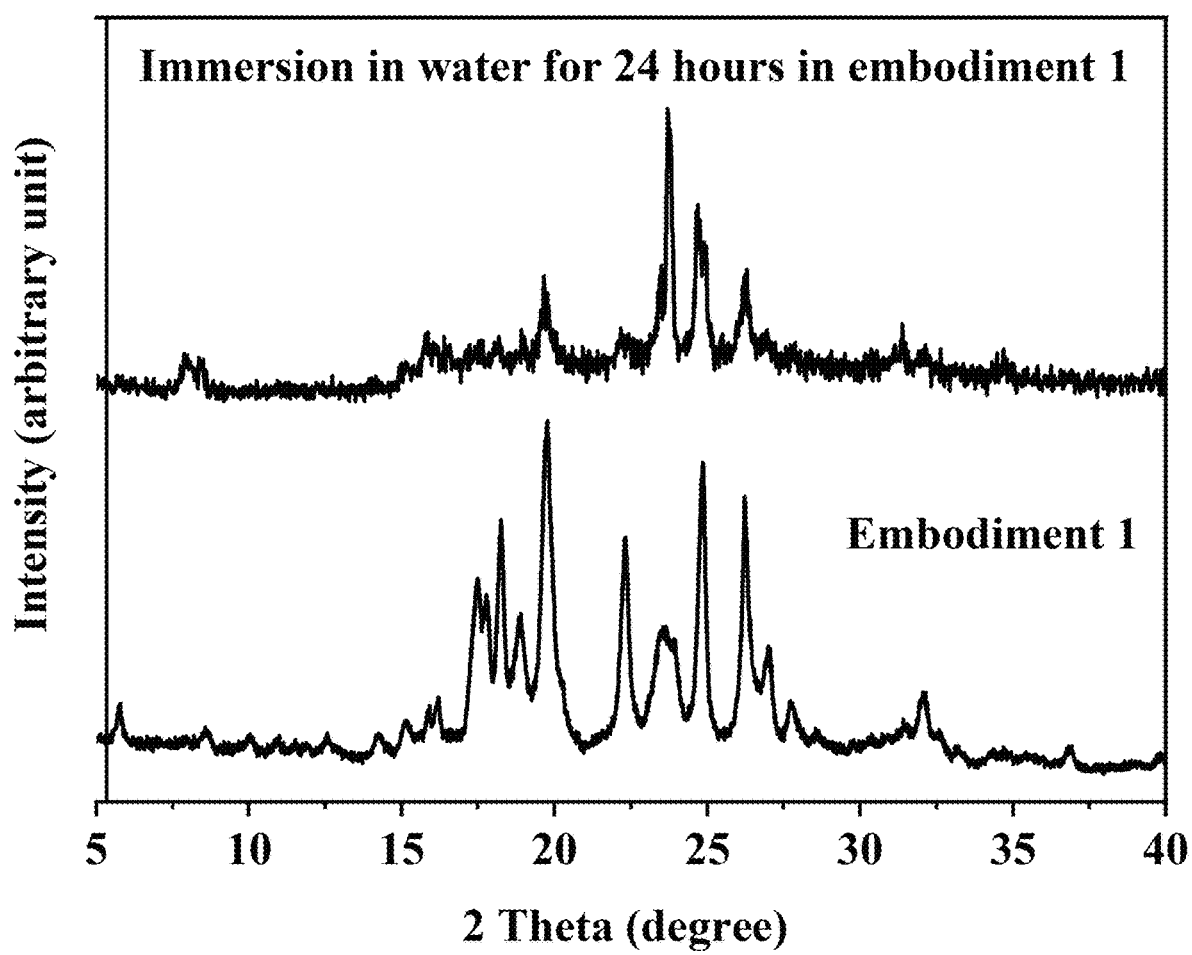
FIG. 7 is the X-ray diffraction spectrum of a hydrogen-bonded organic framework nanosheet prepared in embodiment 1 of the present application before and after being immersed in water for 24 hours.

The XRD spectrum of the hydrogen-bonded organic framework nanosheet prepared in embodiment 1 of the present application after immersion in water is shown in FIG. 7. After immersion in water for 24 hours, the nanosheet is still capable of maintaining its original crystal structure, and water stability of the nanosheet is significantly better than the water stability of comparative examples 1-2.

Crystallographic data of hydrogen-bonded organic framework nanosheet of embodiment 1 and comparative examples 1-2 are obtained by single crystal X-ray diffraction detection. The results are shown in table 1.

TABLE 1

Crystallographic data

| | Comparative example 1 | Comparative example 2 | Embodiment 1 |
|---|---|---|---|
| Chemical formula | $C_{23}H_{25}N_2O_6$ | $C_{20}H_{18}NO_5$ | $C_{34}H_{22}O_8$ |
| Molecular weight | 425.45 | 352.35 | 558.51 |
| Temperature (K) | 296 (2) | 296 (2) | 296 (2) |
| Radiation | 0.71073 | 0.71073 | 0.71073 |
| Syngony | Triclinic | Monoclinic | Monoclinic |
| Space group | $P\bar{1}$ | $P2_1/n$ | C2/c |
| a(Å) | 6.255 (5) | 11.505 (3) | 22.5168 (17) |
| b(Å) | 11.386 (9) | 11.908 (3) | 11.3785 (7) |
| c(Å) | 16.794 (14) | 13.350 (3) | 20.8639 (17) |
| α (°) | 99.97 (2) | 90 | 90 |
| β (°) | 92.32 (2) | 103.335 (6) | 96.783 (3) |
| γ (°) | 102.33 (2) | 90 | 90 |
| V(Å$^3$) | 1147.0 (16) | 1779.6 (8) | 5308.1 (7) |
| Z | 2 | 4 | 8 |
| ρ$_{(calc)}$ (g/cm$^3$) | 1.232 | 1.315 | 1.398 |
| F (000) | 450 | 740 | 2320 |
| Absorption peak (mm$^{-1}$) | 0.090 | 0.095 | 0.100 |
| θ range (deg) | 2.420-27.476 | 2.320-25.141 | 2.188-25.082 |
| Reflns collected | 13241 | 23078 | 28474 |
| | ($R_{int}$ = 0.0768) | ($R_{int}$ = 0.1530) | ($R_{int}$ = 0.1795) |
| Indep. reflns | 5071 | 3181 | 4687 |
| refns obs. [I > 2σ(I)] | 2078 | 1971 | 3299 |
| Data/restr/paras | 5071/2/292 | 3181/2/244 | 4687/4/387 |
| GOF | 1.026 | 0.980 | 1.016 |
| $R_1$/w$R_2$ [I > 2σ(I)] | 0.0641/0.1579 | 0.0565/0.1461 | 0.0514/0.1252 |
| $R_1$/w$R_2$ (all data) | 0.1777/0.2335 | 0.1044/0.1866 | 0.0798/0.1438 |
| Larg peak and hole(e/Å$^3$) | 0.280/-1.94 | 0.326/-0.193 | 0.201/-0.201 |

It can be further confirmed from table 1 that the materials obtained in embodiment 1, comparative example 1 and comparative example 2 have different micro-crystalline structures. As can be seen from table 1, the crystal structure of the hydrogen-bonded organic framework nanosheet prepared by the embodiments of the present application belongs to monoclinic system, C2/c space group, and the cell parameters are A=22.5168, B=11.3785, C=20.8639, α=90, β=96.783, and γ=90, and all carboxyl groups in the microcrystal structure are connected by double hydrogen bonds, and the layered networks of double rhomboids are interpenetrated with each other to form a dense and stable two-dimensional layered structure.

Figure 8A:
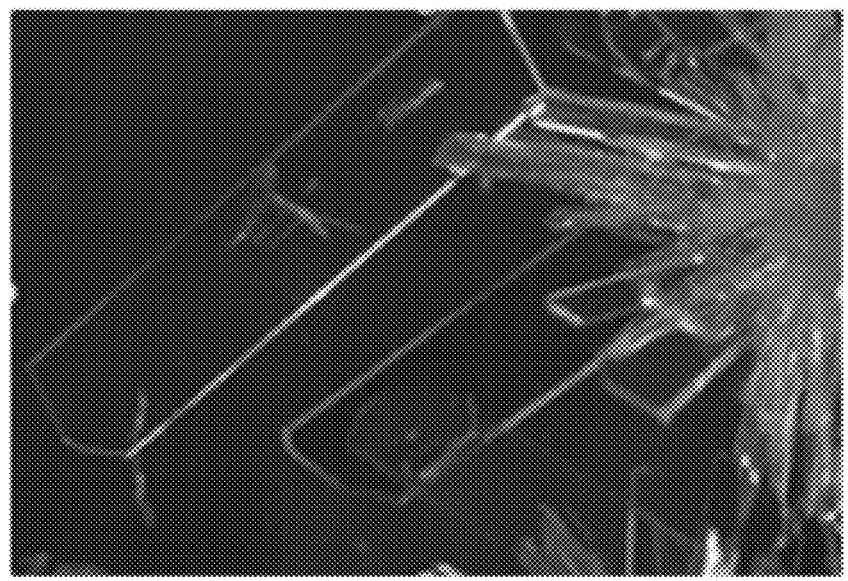
FIG. 8A is an optical microscope photograph of a crystalline material prepared in comparative example 1 of the present application.
Figure 8B:
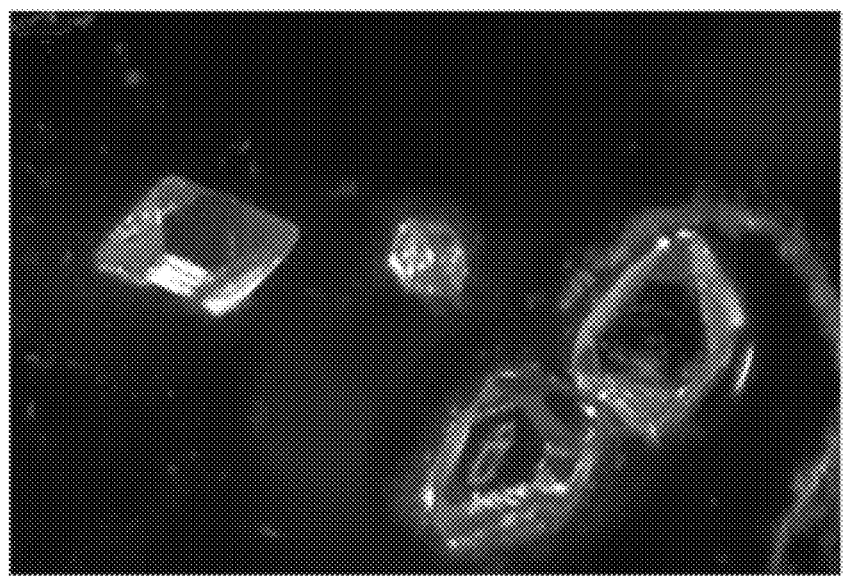
FIG. 8B is an optical microscope photograph of a crystalline material prepared in comparative example 2 of the present application.
Figure 8C:
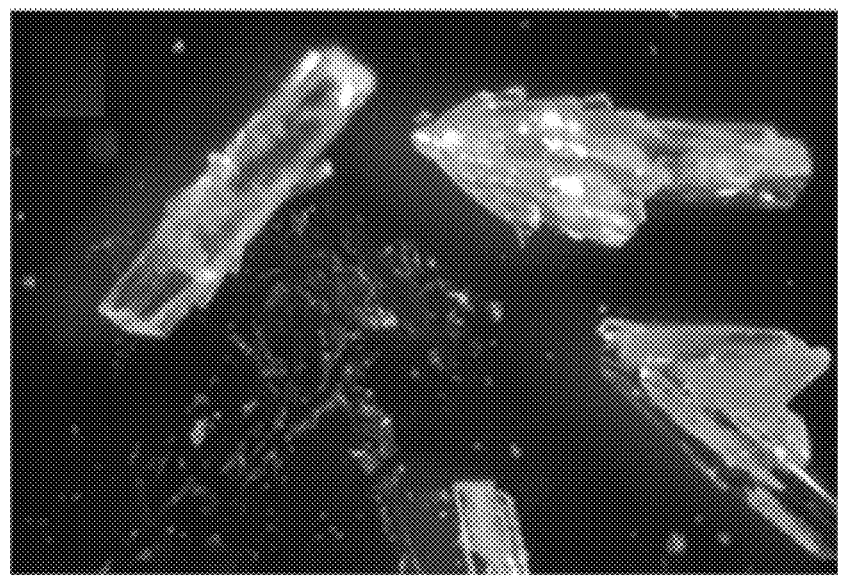
FIG. 8C is an optical microscope photograph of a hydrogen-bonded organic framework nanosheet prepared in embodiment 1 of the present application.
Figure 9A:
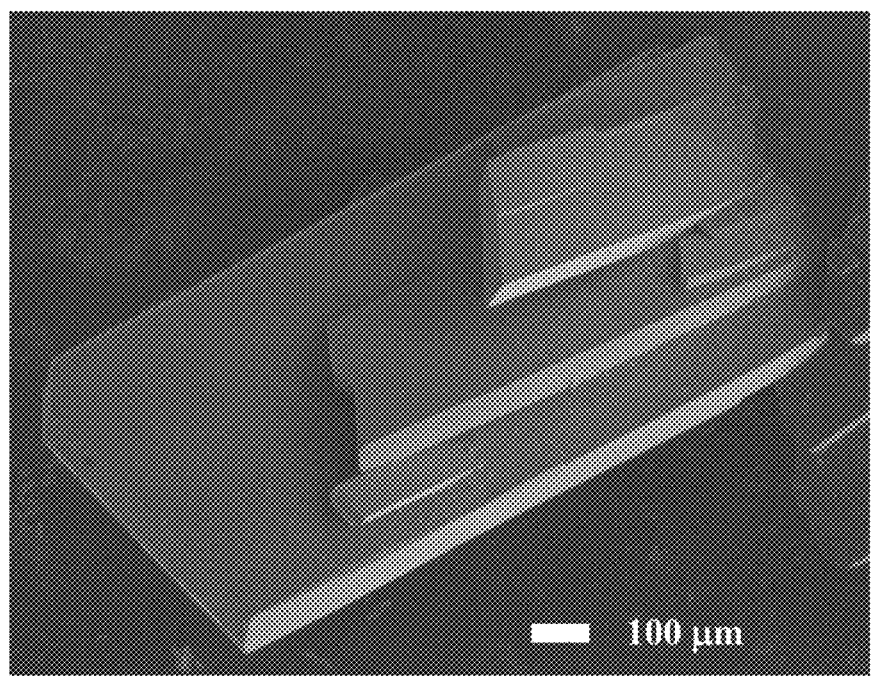
FIG. 9A is a scanning electron microscope photograph of a crystal material prepared in comparative example 1 of the present application.
Figure 9B:
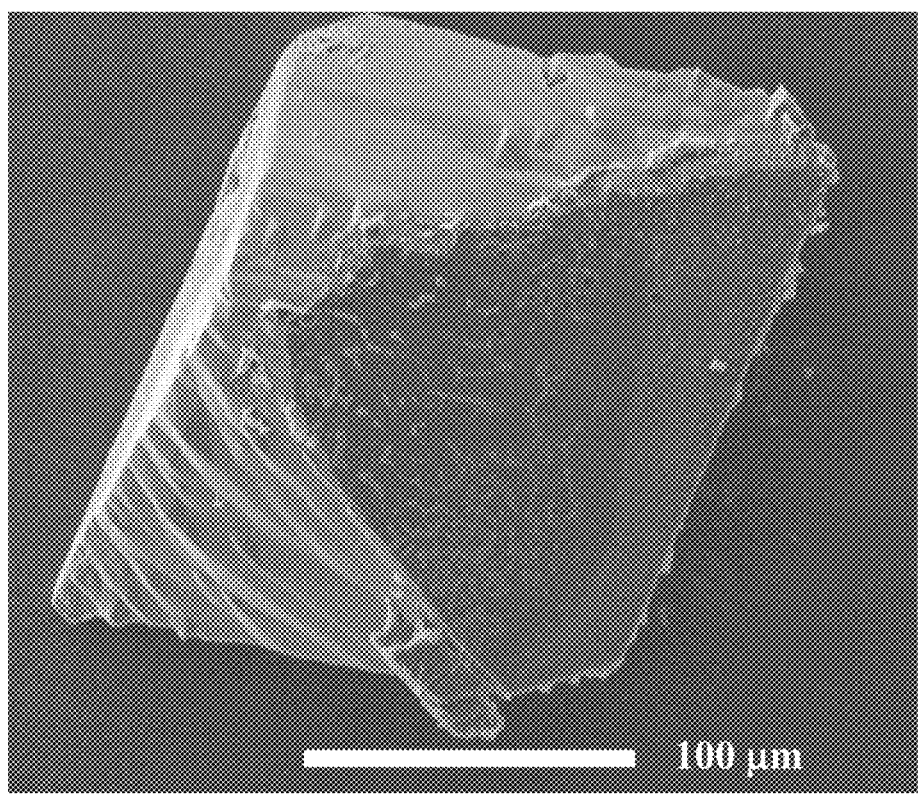
FIG. 9B is a scanning electron microscope photograph of a crystal material prepared in comparative example 2 of the present application.
Figure 9C:
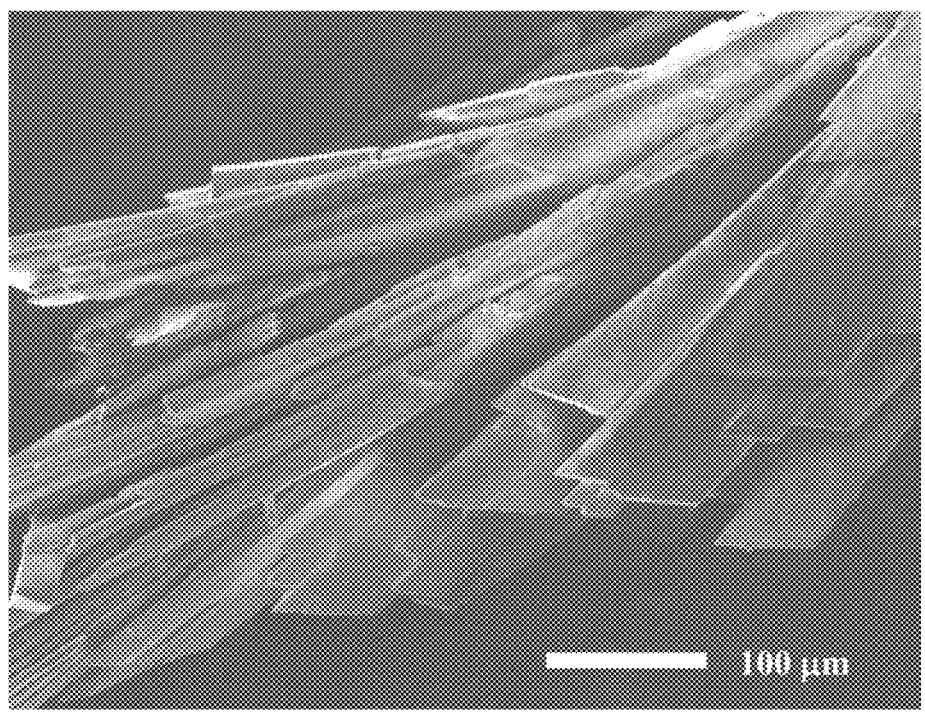
FIG. 9C is a scanning electron microscope photograph of a hydrogen-bonded organic framework nanosheet prepared in embodiment 1 of the present application.
Figure 10:
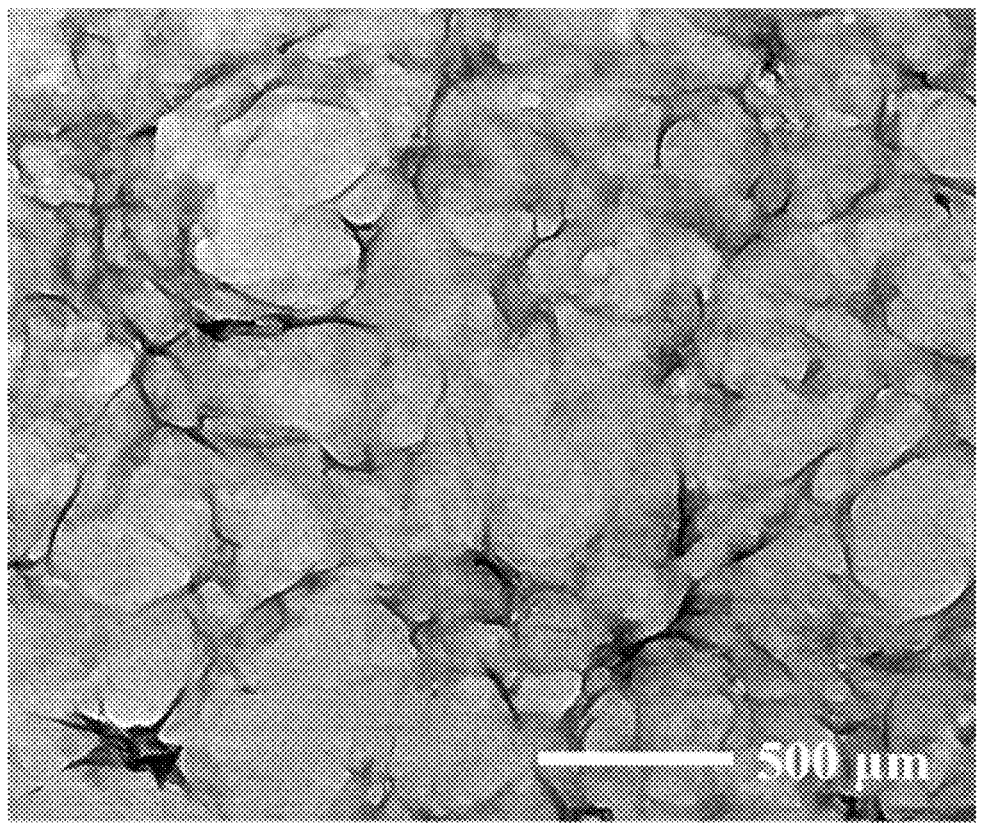
FIG. 10 is a transmission electron microscope photograph of a hydrogen-bonded organic framework nanosheet prepared in embodiment 1 of the present application.
Figure 11:
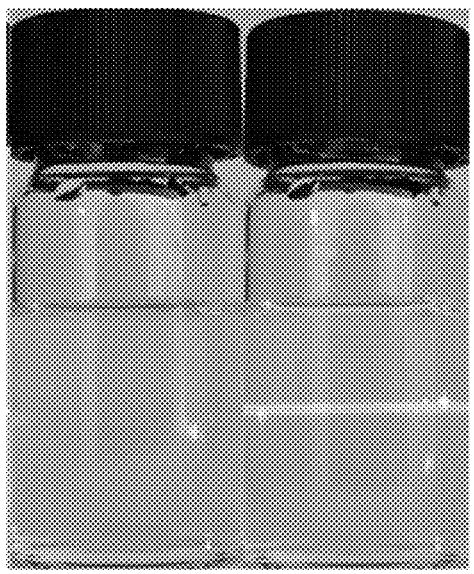
FIG. 11 is a Tyndall effect photograph of a dispersion of a hydrogen-bonded organic framework nanosheet fluorescent probe in water prepared in embodiment 1 of the present application.
Figure 12A:
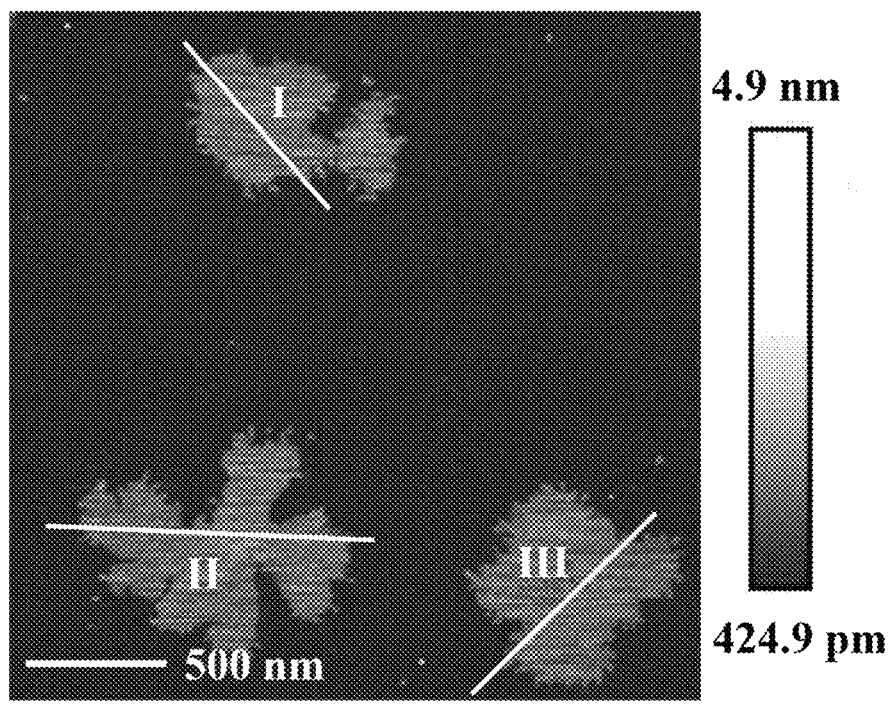
FIG. 12A is a height sensor picture from atomic force microscope photograph of a hydrogen-bonded organic framework nanosheet prepared in embodiment 1 of the present application and height profiles measured along the corresponding track (I, II, III).
Figure 12B:
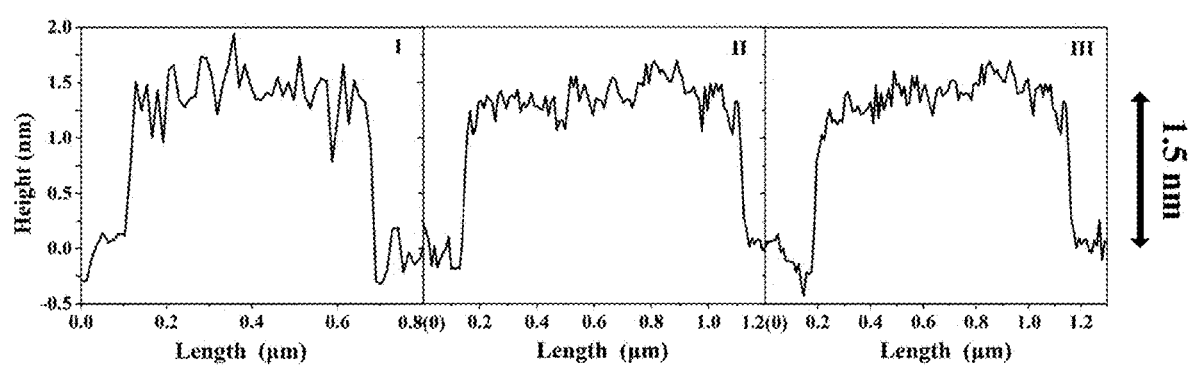
FIG. 12B is a height profiles measured along the corresponding track (I, II, III) in FIG. 12A of a hydrogen-bonded organic framework nanosheet prepared in embodiment 1 of the present application.

The optical microscope photograph of the hydrogen-bonded organic framework nanosheet prepared in embodiment 1 of the present application and the crystal materials prepared in comparative examples 1-2 are shown in FIG. 8A, FIG. 8B and FIG. 8C, and the scanning electron microscope photograph are shown in FIG. 9A, FIG. 9B, and FIG. 9C, where FIG. 9A is comparative example 1, FIG. 9B is comparative example 2, and FIG. 9C is embodiment 1. The transmission electron microscope (TEM) photograph of the hydrogen-bonded organic framework nanosheet prepared in embodiment 1 of the present application is shown in FIG. 10, and the Tyndall effect photo of the hydrogen-bonded organic framework nanosheet fluorescent probe dispersed in water prepared in embodiment 1 of the present application is shown in FIG. 11. The atomic force microscope photos and height profiles of hydrogen-bonded organic framework nanosheet prepared in embodiment 1 of the present application are shown in FIG. 12A and FIG. 12B. FIG. 12A is a height sensor picture from an atomic force microscope photograph a hydrogen-bonded organic framework nanosheet prepared in embodiment 1 of the present application and height profiles measured along the corresponding track (I, II, III). FIG. 12B is height profiles measured along the corresponding track (I, II, III) in FIG. 12A of a hydrogen-bonded organic framework nanosheet prepared in embodiment 1 of the present application. As can be seen from FIG. 7, FIG. 8A, FIG. 8B, FIG. 8C, FIG. 9A, FIG. 9B, FIG. 9C, FIG. 10, FIG. 11, FIG. 12A, and FIG. 12B, the HOFs material prepared by the embodiments of the application has excellent water stability in the crystal structure, and has an ultra-thin two-dimensional nano-sheet structure with a thickness of only about 1.5 nanometers. This is due to the double hydrogen bond structure and the planar network topology of double interpenetration which are different from comparative examples 1 and 2.

Performance Test

Detection of Uranyl Ions in Water Environment

Figure 13:
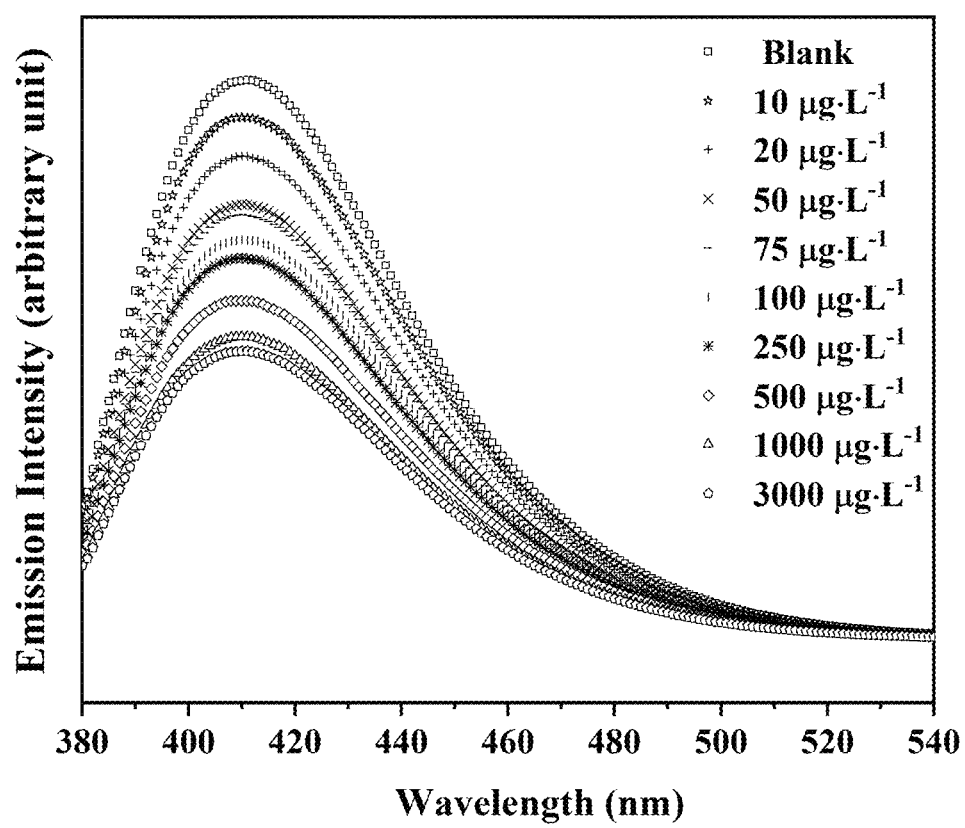
FIG. 13 shows a fluorescence spectra of a hydrogen-bonded organic framework nanosheet fluorescent probe prepared in embodiment 1 of the present application in uranyl solutions with different concentrations.
Figure 14:
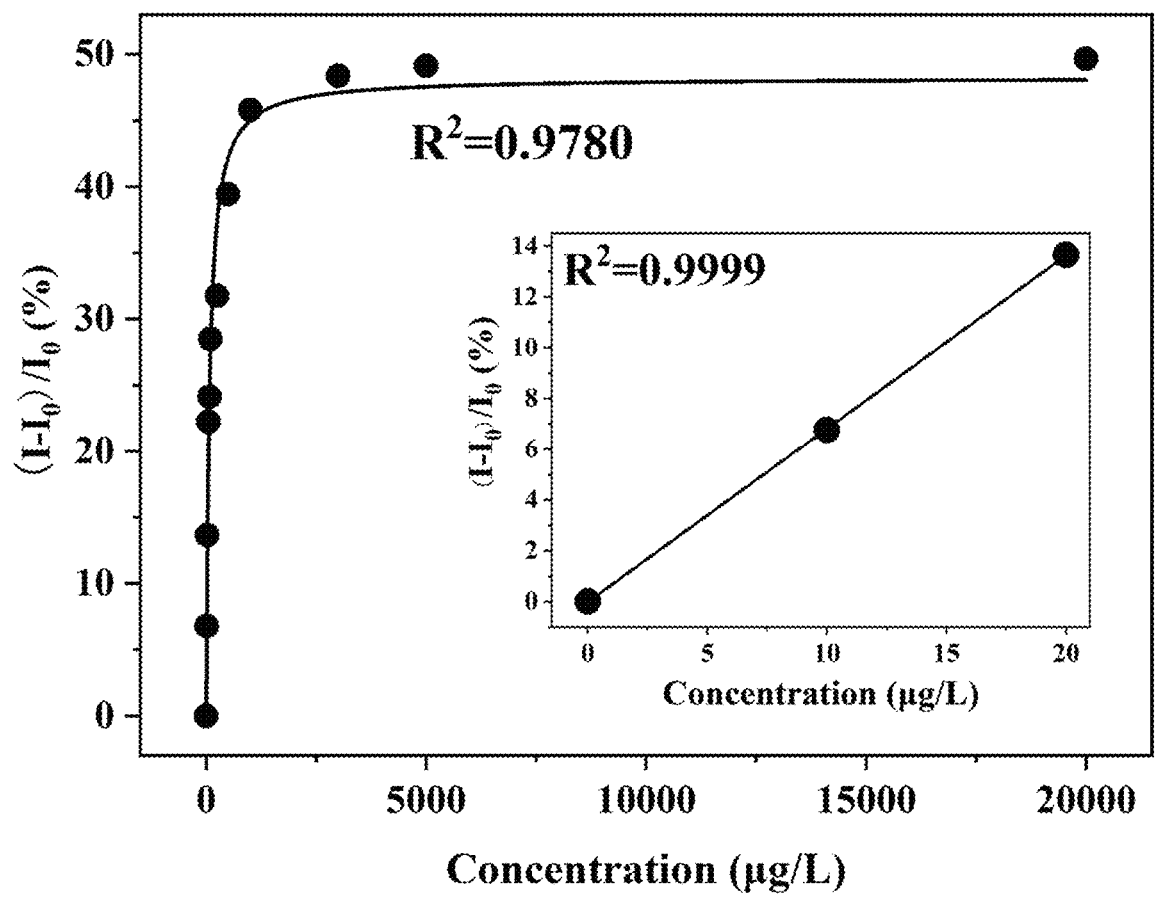
FIG. 14 is a fitting curve of a relationship between fluorescence emission intensity and uranyl concentration of a hydrogen-bonded organic framework nanosheet fluorescent probe prepared in embodiment 1 of the present application.

The fluorescent probe prepared in embodiment 1 are fully mixed with uranyl solution with a concentration of 0-400 mg/L, respectively, according to the volume ratio of 1:1, and then stood for 30 minutes. Before spectrum collection, the fluorescent probe is ultrasonically to suspension liquid for uniform dispersing. A fluorescence spectrometer is used to detect the fluorescence spectrum of the above-mentioned liquid, the excitation wavelength is set as 363 nm, and the fluorescence spectrum is measured as shown in FIG. 13. The solution shows a fluorescence emission peak at the wavelength of 410 nm, and the higher the concentration of uranyl ion in the aqueous solution, the lower the fluorescence emission intensity of the probe solution. The lowest detection limit is 0.13 g/L calculated by a fluorescence emission intensity-uranyl ion concentration fitting curve (FIG. 14) and formula DT=3σ/slopeσ=100×($I_{SE}/I_0$), where DT is the detection limit, $I_{SE}$ is the standard error of the emission intensity, $I_0$ is determined by the blank sample at the maximum excitation wavelength in deionized water, and the slope is obtained by fitting the uranyl concentration-dependent luminescence intensity curve at low concentration.

Figure 15:
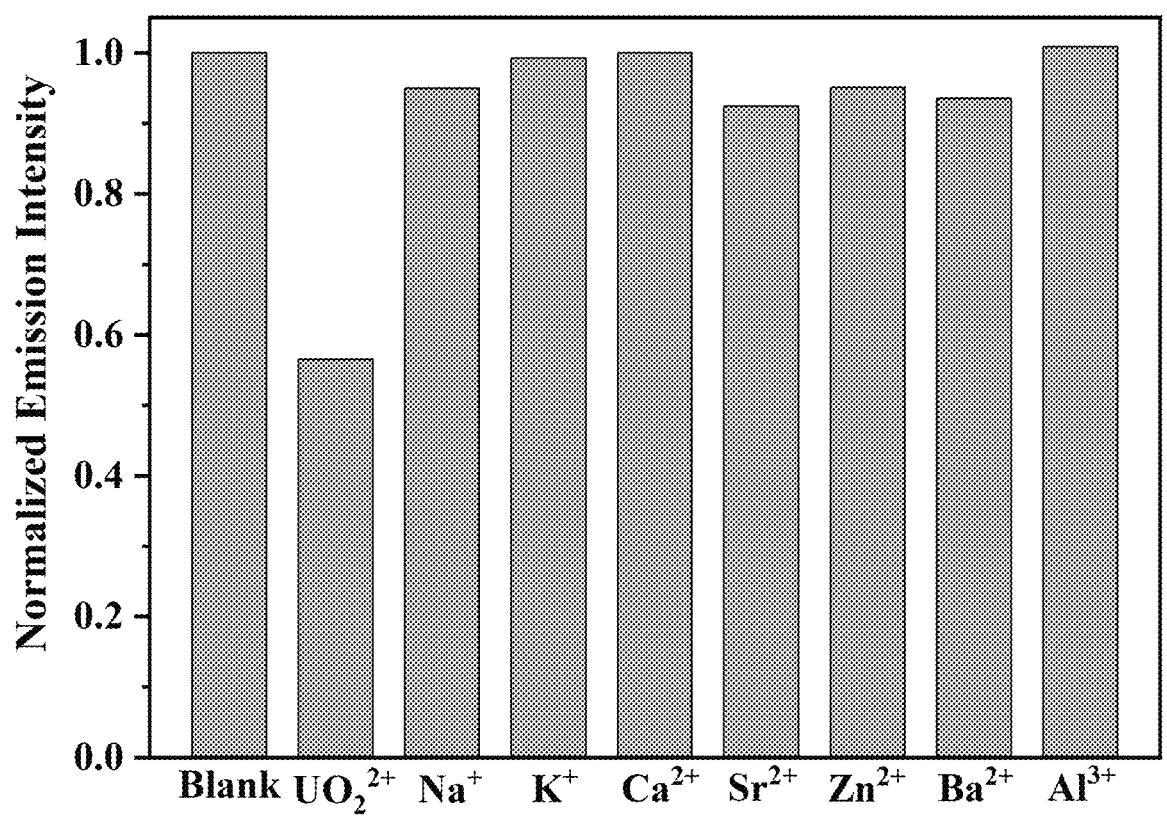
FIG. 15 is selective data of fluorescence quenching response of a hydrogen-bonded organic framework nanosheet prepared in embodiment 1 of the present application to uranyl ions.

FIG. 15 shows the comparison of the fluorescence emission intensity of the hydrogen-bonded organic framework nanosheet fluorescent probe prepared in embodiment 1 of the present application in the solution containing different metal ions. It can be seen that the quenching reaction of fluorescent probe does not occur in water with other metal ions except uranyl ions. It shows that the hydrogen-bonded organic framework nanosheet fluorescent probe prepared in embodiment 1 has good selectivity for the quenching response of uranyl. The above-mentioned embodiments only describe the preferred mode of the application, and do not limit the scope of the application. Under the premise of not departing from the design spirit of the application, various modifications and improvements made by ordinary technicians in the field to the technical scheme of the application shall fall within the protection scope determined by the claims of the application.

What is claimed is:

1. A preparation method of a hydrogen-bonded organic framework nanosheet, comprising following steps:
   mixing and dissolving 1,2,4,5-tetrakis (4-carboxyphenyl) benzene with N,N-dimethylformamide in a container, placing the container uncapped in a large container filled with water, sealing the large container, followed by standing and heating, suction filtering to obtain colorless crystals, drying to obtain a solid material, grinding and dispersing the solid material in a solvent, performing ultrasonication in an ice-water bath condition, centrifuging to discard supernatant, and drying to obtain the hydrogen-bonded organic framework nanosheet;
   wherein the 1,2,4,5-tetrakis (4-carboxyphenyl) benzene is mixed with the N, N-dimethylformamide, and heated to dissolve solid, so a concentration of the 1,2,4,5-tetrakis (4-carboxyphenyl) benzene is 1-50 mg/mL;
   a temperature for the standing and heating is more than or equal to 100° C.;
   a duration for the standing is 1-7 days;
   after the suction filtering to obtain the colorless crystals, a temperature for the drying is 60-200° C.

2. The preparation method according to claim 1, wherein the solvent comprises one or more of ethanol, water, methanol and isopropanol.

3. A hydrogen-bonded organic framework nanosheet prepared by the preparation method according to claim 1, wherein a crystal structure of the hydrogen-bonded organic framework nanosheet belongs to a monoclinic system, C2/c space group, and cell parameters are a=22.5168, b=11.3785, c=20.8639, α=90, β=96.783, γ=90, all carboxyl groups in a micro-crystal structure are connected by double hydrogen bonds, and layered networks of double rhomboids are interpenetrated with each other to form a dense and stable two-dimensional layered structure.

4. An application of the hydrogen-bonded organic framework nanosheet according to claim 3, wherein the hydrogen-bonded organic framework nanosheet is applied in a detection of uranyl ions.

5. The application according to claim 4, wherein the hydrogen-bonded organic skeleton nanosheet is prepared to obtain a fluorescent probe, and the fluorescent probe is applied in the detection of uranyl ions.

6. The application according to claim 5, wherein a preparation method of the fluorescent probe comprises steps of grinding the hydrogen-bonded organic framework nanosheet for 10 minutes, followed by placing in a solvent, and ultrasonically dispersing for 1-10 minutes to obtain the fluorescent probe with a concentration of 10-200 mg/L.

* * * * *